United States Patent
Schaefer

(10) Patent No.: US 10,993,723 B2
(45) Date of Patent: May 4, 2021

(54) MEDICAL IMPLANT FOR CLOSURE OF A DEFECT APERTURE, A VESSEL, AN ORGAN PATH OR ANOTHER APERTURE IN A HUMAN OR ANIMAL BODY

(71) Applicant: PFM MEDICAL AG, Cologne (DE)

(72) Inventor: Joachim Schaefer, Nonnweiler (DE)

(73) Assignee: PFM MEDICAL AG, Cologne (DE)

( * ) Notice: Subject to any disclaimer, the term of this patent is extended or adjusted under 35 U.S.C. 154(b) by 262 days.

(21) Appl. No.: 15/568,983

(22) PCT Filed: Feb. 19, 2016

(86) PCT No.: PCT/EP2016/053547
§ 371 (c)(1),
(2) Date: Oct. 24, 2017

(87) PCT Pub. No.: WO2016/169671
PCT Pub. Date: Oct. 27, 2016

(65) Prior Publication Data
US 2018/0125498 A1    May 10, 2018

(30) Foreign Application Priority Data
Apr. 24, 2015   (DE) .................. 20 2015 102 060.0

(51) Int. Cl.
*A61B 17/12*  (2006.01)
*A61B 17/00*  (2006.01)
*A61M 25/10*  (2013.01)

(52) U.S. Cl.
CPC .... *A61B 17/12109* (2013.01); *A61B 17/1215* (2013.01); *A61B 17/12145* (2013.01);
(Continued)

(58) Field of Classification Search
CPC ........ A61B 17/12109; A61B 17/12145; A61B 17/1215; A61B 2017/00867;
(Continued)

(56) References Cited

U.S. PATENT DOCUMENTS 5,304,194 A * 4/1994 Chee ................ A61B 17/12022
604/104
5,382,260 A * 1/1995 Dormandy, Jr. ..........................
A61B 17/12022
604/104
(Continued)

FOREIGN PATENT DOCUMENTS

DE    69826275    11/2005
DE    69831889    4/2006
(Continued)

OTHER PUBLICATIONS

International Search Report from corresponding PCT Appln. No. PCT/EP2016/053547. dated Jun. 3, 2016.

*Primary Examiner* — Phong Son H Dang
(74) *Attorney, Agent, or Firm* — Grossman, Tucker, Perreault & Pfleger, PLLC

(57) ABSTRACT

The invention relates to a medical implant for closure of a defect aperture, a vessel, an organ path or another aperture in a human or animal body, comprising a base body and at least one fibre, wherein the base body can be reversibly transformed against elastic material forces from a secondary shape into a primary shape, wherein in the primary shape the base body has an elongated shape and in the secondary shape is at least partially coiled and comprises a cone shape, which is characterized in that the at least one fibre is connected to the base body such that the fibre in the secondary shape of the base body extends at least once, preferably a plurality of times, transversely through the cone shape.

17 Claims, 3 Drawing Sheets

(52) U.S. Cl.
CPC ..... *A61B 17/0057* (2013.01); *A61B 17/12136* (2013.01); *A61B 2017/00867* (2013.01); *A61B 2017/1205* (2013.01); *A61M 25/10* (2013.01)

(58) Field of Classification Search
CPC ...... A61B 17/12136; A61B 2017/1205; A61B 17/0057; A61M 25/10
See application file for complete search history.

(56) References Cited

U.S. PATENT DOCUMENTS

| | | | | |
|---|---|---|---|---|
| 5,649,949 | A * | 7/1997 | Wallace | A61B 17/12022 600/200 |
| 5,792,154 | A * | 8/1998 | Doan | A61B 17/12022 606/151 |
| 5,911,717 | A | 6/1999 | Jacobsen et al. | |
| 6,013,084 | A | 1/2000 | Ken et al. | |
| 6,024,765 | A * | 2/2000 | Wallace | A61B 17/12022 606/191 |
| 6,143,007 | A * | 11/2000 | Mariant | A61B 17/1215 606/151 |
| 6,159,165 | A | 12/2000 | Ferrera et al. | |
| 6,187,027 | B1 | 2/2001 | Mariant et al. | |
| 7,896,899 | B2 * | 3/2011 | Patterson | A61L 31/128 606/200 |
| 8,545,573 | B2 * | 10/2013 | Matthews | A61B 17/1215 623/23.72 |
| 9,301,764 | B2 * | 4/2016 | White, Jr. | A61B 17/1215 |
| 10,182,822 | B2 * | 1/2019 | Freudenthal | A61B 17/12154 |
| 2005/0004598 | A1 * | 1/2005 | White, Jr. | A61B 17/1215 606/200 |
| 2005/0187564 | A1 * | 8/2005 | Jayaraman | A61B 17/12022 606/141 |
| 2006/0036281 | A1 * | 2/2006 | Patterson | A61B 17/12022 606/200 |
| 2006/0224183 | A1 | 10/2006 | Freudenthal | |
| 2011/0295303 | A1 * | 12/2011 | Freudenthal | A61B 17/12022 606/200 |
| 2016/0166257 | A1 * | 6/2016 | Allen | A61B 17/12113 606/200 |

FOREIGN PATENT DOCUMENTS

| | | | | |
|---|---|---|---|---|
| DE | 69833699 | | 8/2006 | |
| DE | 602004008301 | | 5/2008 | |
| DE | 102007038446 | | 2/2009 | |
| DE | 102007038446 | A1 * | 2/2009 | ....... A61B 17/12022 |
| EP | 0778005 | | 6/1997 | |
| EP | 0750480 | | 9/2004 | |
| EP | 1584298 | | 10/2005 | |
| JP | H8-131553 | | 5/1996 | |
| JP | H9-276280 | | 10/1997 | |
| JP | 2001-079011 | | 3/2001 | |
| JP | 2005-237952 | | 9/2005 | |
| WO | 95/25480 | | 9/1995 | |
| WO | 01/49185 | | 7/2001 | |
| WO | 2004/064671 | | 8/2004 | |

* cited by examiner

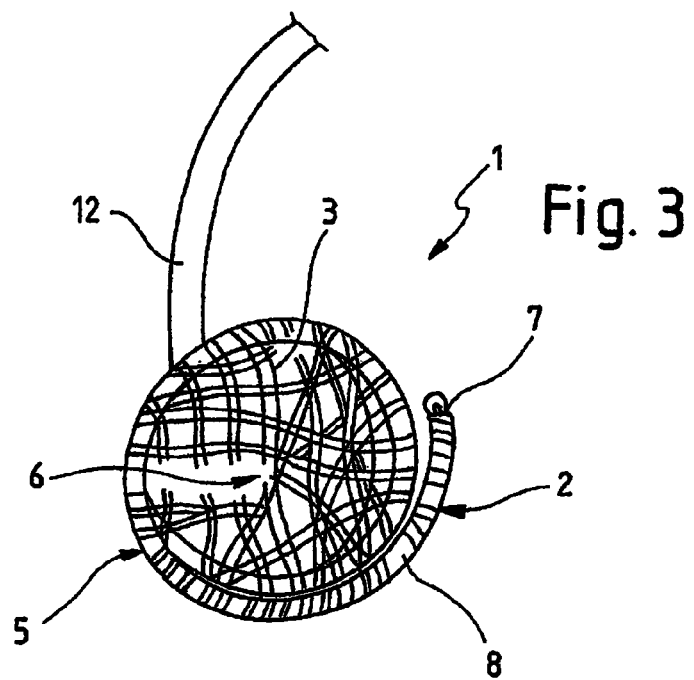
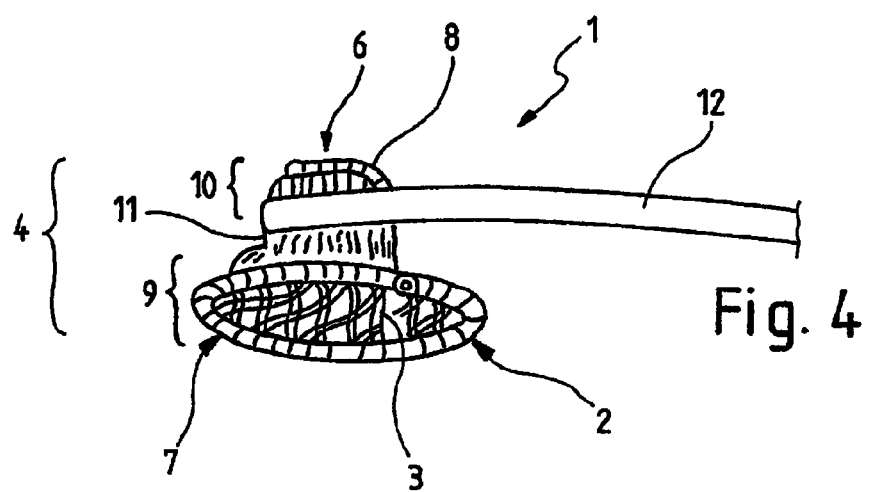

MEDICAL IMPLANT FOR CLOSURE OF A DEFECT APERTURE, A VESSEL, AN ORGAN PATH OR ANOTHER APERTURE IN A HUMAN OR ANIMAL BODY

FIELD

The invention relates to a medical implant for closure of a defect aperture, a vessel, an organ path or another aperture in a human or animal body. The medical implant according to the invention comprises a base body and at least one fibre. Medical implants for closure of defect apertures, vessels, organ paths or other apertures in a human or animal body are known in various forms. Such medical implants are, for example, expanded at a desired location by means of a balloon catheter or consist of a self-expanding material such as, for example, a form memory material. Preferably, the medical implant is implanted into the human or animal body via a catheter by means of a minimally invasive method.

BACKGROUND

During transport of the medical implant through the catheter to the desired location in the human or animal body, the medical implant has a primary shape which is substantially elongated. The medical implant therefore has a large ratio of longitudinal expansion to transverse expansion in the primary shape. Upon exiting the catheter, the medical implant takes a secondary shape to close the defect aperture, vessel, organ path, or other aperture of the human or animal body. From the prior art, a plurality of secondary shapes are known to close the organ pathway or the other aperture of the human or animal body. For example, the base body of a medical implant is designed in the secondary shape in such a way that the base body has a funnel shape.

It is also known to provide thrombogenic fibres to the medical implant in order to improve an embolization effect.

For this purpose for example, EP 0 750 480 B1 discloses that thrombogenic fibres of commercially available Z-twist-dacron fibre material are arranged at regular intervals along the length of the windings of a spiral between closely adjacent windings. These thrombogenic fibres then protrude radially between the windings from the primary spiral. A similar structure is also known from JP-8131553. Also JP-2001079011 provides a similar structure. According to DE 698 31 889 T2 a medical implant is disclosed in which a resilient coil-shaped wound wire is provided on its outer surface with cuts which on the one hand serve to improve the flexibility of the coil wire and, on the other hand, to the attaching of thrombogenic fibres. The fibres may be knotted into the wire, attached there by means of an adhesive, fused or by another bonding method.

According to DE 698 26 275 T2 a medical implant is proposed which has a primary spiral which can be shaped into various secondary shapes. Thrombogenic fibres are interwoven along the primary spiral. These are each fastened at one end to a winding and threaded through some of the intermediate windings so that loops of the thrombogenic fibres protrude on the outer side of the primary spiral. Alternatively, it is disclosed to provide a braided sheath of a fibrous material surrounding the primary spiral. DE 698 33 699 T2 discloses a similar construction, in which thrombogenic fibres are likewise threaded through the helix of a primary spiral or a secondary spiral. In this case, loops of thrombogenic fibres also protrude from the spiral. The vessel closure spiral according to DE 698 26 275 T2 also shows a corresponding design.

From the circumference of the coil or spiral protruding fibres are also known from U.S. Pat. No. 6,187,027 B1, EP 1 584 298 A1, JP-2005237952, JP-8131553 and JP-2001079011.

A further alternative solution for applying thrombogenic fibres to an occlusion spiral is described in EP 0 778 005 A1 and JP-9276280. In this case a multiplicity of strands of thrombogenic fibres are passed inside through the helix of the occlusion spiral. The ends of the thrombogenic fibre strands are connected to one another.

Furthermore, DE 10 2007 038 446 A1 discloses a medical implant in which thrombogenic fibres are wound around the spiral base body.

A further medical implant for the closure of a defect aperture, a vessel, an organ pathway or another aperture in a human or animal body is marketed by pfm medical ag under the designation "Nit-Occlud VSD". This medical implant comprises a base body and a plurality of thrombogenic fibres. The base body can be reversibly transformed against elastic restoring forces from a secondary shape into a primary shape, wherein in the primary shape the base body has an elongated shape with a large ratio of longitudinal expansion to transverse expansion and in the secondary shape is at least partially coiled shape with a smaller ratio of longitudinal expansion to transverse expansion than in the primary shape. The Nit-Occlud Lê VSD spiral is a permanent implant for the closure of ventricular septal defects (VSD), which is guided into the heart chamber by means of minimally invasive catheter technology. The spiral consists of nitinol, a material with shape memory, and has the shape of a cone in the relaxed state (secondary shape).

In order to achieve an accelerated thrombogenicity and thus also a shorter closure time, thrombogenic fibres are provided in the distal region of the Nit-Occlud Lê VSD spiral, i.e. in the region of the cone with the larger diameter. Therefore, a plurality of short thrombogenic fibres are attached to the base body. In this case, the individual thrombogenic fibres consist of a plurality of individual filaments which are linked to one another or are entangled in the middle region of the thrombogenic fibres and are free at the ends of the thrombogenic fibres. For example, the thrombogenic fibres of the Nit-Occlud Lê VSD spiral are approximately 1 cm long. Depending on the size of the VSD spiral, approximately 10 to 150 thrombogenic fibres are provided, wherein each thrombogenic fibre has for example 34 or 36 individual filaments. However, it has been found that the thrombogenic fibres can stick to the VSD spiral in a wet state in such a way that an aperture remains in the tapered region of the cone, that is to say in the narrow funnel region. This increases the closure time. It is therefore an object of the present invention to improve the medical implants known from the prior art for closing a defect aperture, a vessel, an organ path or another aperture in a human or animal body with a base body and fibres with regard to the closure time.

SUMMARY

According to the invention, the object is achieved by means of a medical implant for closure of a defect aperture, a vessel, an organ path or another aperture in a human or animal body, comprising a base body and at least one fibre, wherein the base body can be reversibly transformed against elastic material forces from secondary shape into a primary shape, wherein in the primary shape the base body has an elongated shape and in the secondary shape is at least partially coiled and comprises a cone shape, which is characterized in that the at least one fibre is connected to the base body such that the fibre in the secondary shape of the base body extends at least once, preferably a plurality of times, transversely through the cone shape.

The invention is based on the findings that the at least one fibre of the medical implant cannot stick to the inner wall of the cone shape in the wet state in such a way that an aperture remains in the tapered region of the cone shape if the at least one fibre extends transversely through the cone shape.

In the primary shape the base body has an elongated shape so that it can be implanted into the human or animal body by means of a minimally invasive catheter technique. In this primary shape, the base body has a large ratio of longitudinal expansion to transverse expansion.

When leaving the catheter used for implantation the base body preferably assumes independently the secondary shape, in which the medical implant formed from the base body closes the defect aperture, the vessel, the organ path or the other body aperture in the human or animal body. In this secondary shape the base body has a smaller ratio of longitudinal expansion to transverse expansion than in the primary shape.

A cone shape in the sense of the invention comprises an extended region and a tapered region. The cone shape thus corresponds to a funnel shape. Preferably, the extended region of the cone shape is located at the distal end of the medical implant and the tapered region of the cone shape is located at the proximal end of the medical implant. Distal in the sense of the invention is the region facing the body center and proximal in the sense of the invention is the region of the medical implant facing away from the body center.

Furthermore, the design of the medical implant according to the invention has a reduced hemolysis risk because the number of fibres used has been significantly reduced. The loose ends of the fibres can contribute to the destruction of erythrocytes, which is an important factor in hemolysis.

A fibre in the sense of the invention is a fine, thin filament-like structure which consists of a vegetable or animal raw material or is synthetically produced.

According to a preferred variant of the invention the at least one fibre extends at least once through the center of the cone shape. If the medical implant is implanted in the human or animal body, in particular into a vessel or organ, wherein the medical implant is in connection with the blood circulation, increased flow velocities occur in the region of the tapered region. In order that the at least one fibre does not change its position in such a way that an aperture remains in the tapered region because of the increased flow velocities, the at least one fibre passes at least once through the center of the conical shape.

In a variant of the invention the at least one fibre forms a net-like structure in the cone shape. Such a net-like structure results in increased thrombogenicity and, consequently, reduced closure speed. Furthermore, a net-like structure has the advantage that the individual struts of the net-like structure are mutually supported so that the abovementioned increased flow velocities cause virtually no modifications of the net-like structure.

According to a further advantageous variant of the invention the at least one fibre is connected to the base body at at least two points. Such a configuration leads in a simple manner to the fact that the at least one fibre extends in the secondary shape of the base body at least once transversely through the cone shape. Furthermore, the at least one fibre runs almost parallel to the base body in the primary shape of the base body so that the at least one fibre has virtually no influence on the diameter of the medical implant in the primary shape. The diameter of the medical implant in the primary shape is particularly important for minimally invasive implantation since the diameter of the medical implant decisively influences the size of the catheter to be used.

In an advantageous variant the at least one fibre is connected to the base body at more than two points. Thus, the at least one fibre is arranged in the primary shape of the base body in a wavy manner on or around the base body and the regions of the at least one fibre which are not connected to the base body extend transversely through the cone shape in the secondary shape.

The distance between the at least two points at which the thrombogenic fibre is connected to the base body is preferably between 0.1 and 2.0 cm and in particular between 1.0 and 1.5 cm. According to an advantageous variant of the invention the at least one fibre projects at most 0.5 cm from the base body in the primary shape of the base body. This is particularly advantageous for an implantation of the implant according to the invention by means of a minimally invasive catheter technique.

According to a particularly advantageous variant of the invention at least two fibres are each connected to the base body at at least two points. Again, the distance between the individual connecting points of a fibre with the base body is preferably between 0.1 and 2.0 cm and in particular between 1.0 and 1.5 cm.

According to a variant of the invention the connecting points of the respective fibres are spaced from one another, preferably at a regular distance. As a result, a structure is achieved in the secondary shape in which the individual elements extending transversely through the cone shape mutually support one another.

The base body is advantageously made of a material with a shape memory, in particular of nitinol or a plastic with a shape memory. As a result, the base body can unfold or wind itself autonomously from the primary shape into the secondary shape when leaving the implantation catheter.

According to a variant of the invention the base body is formed from a wire-like element, wherein the base body having the form of a helix. As a result, the base body exhibits a high degree of flexibility and at the same time sufficient stability to adopt a coiled cone shape in the secondary shape.

Advantageously, an inner mandrel is arranged in the interior of the cylindrically shaped base body. By means of the inner mandrel the medical implant can be for example transferred in a simple manner into which the primary shape.

According to a variant of the invention the cone shape consists of two funnels inserted into each other. This improves the stability of the medical implant in the secondary shape.

In a particularly preferred variant of the invention the at least one fibre is a thrombogenic fibre.

According to a variant of the invention the at least one thrombogenic fibre consists of a plastic fibre, for example selected from the group comprising absorbing and nonabsorbing materials, natural and synthetic substances, in particular polyesters, polyamides, polypropylene, polybutyl esters, expanded polytetrafluoroethylene (ePTFE), polyvinyldifluoroethylene (PVDF), Nylon, linen, silk, catgut.

According to an advantageous variant of the invention the coiled secondary shape has a first tapered region, a cylindrical region with smaller diameter adjoining the end of the latter, and a third region at least partially extending around the outer surface of the first tapered region toward the end of the first tapered region with the extended diameter.

In a variant according to the invention the medical implant in the secondary shape has a diameter between 2.0 and 20.0 mm in the extended region, preferably between 8.0 and 16.0 mm. In the tapered region the medical implant in the secondary shape has, for example, a diameter between 1.0 and 10.0 mm, preferably between 6.0 and 8.0 mm.

The cylindrical region of a variant of the invention has, for example, a diameter between 1.0 and 7.0 mm, preferably between 5.0 and 6.5 mm.

BRIEF DESCRIPTION OF THE DRAWINGS

The invention is explained in more detail below with reference to the exemplary embodiments shown in the figures. It shows:

FIG. 3 is a perspective view of the medical implant from FIGS. 1 and 2 in the secondary shape, FIG. 4 is a further perspective view of the medical implant from FIG. 3 in the secondary shape.

DETAILED DESCRIPTION

Figure 1:
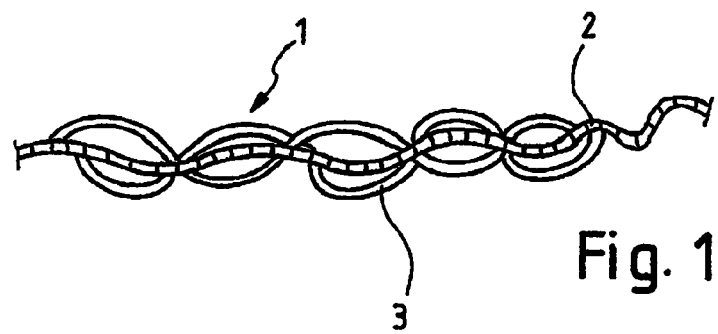
FIG. 1 is a perspective view of a medical implant according to the invention in a primary shape.

FIG. 1 shows a perspective view of a medical implant 1 according to the invention for closure of a defect aperture, a vessel, an organ path or another aperture in a human or animal body. The medical implant 1 of FIG. 1 comprises a base body 2 and at least one fibre 3, wherein the fibre 3 preferably being thrombogenic. Even though the invention is explained below in connection with at least one thrombogenic fibre, other types of fibres can in principle also be used.

The base body 2 can be reversibly converted against elastic material forces from a secondary shape to a primary shape. In the primary shape the base body 2 has an elongated shape and in the secondary shape the base body 2 is at least partly coiled and has a cone shape 4.

The medical implant 1 according to the invention is characterized in that the at least one thrombogenic fibre 3 is connected to the base body 2 such that the thrombogenic fibre 3 in the secondary shape of the base body 2 extends at least once, preferably several times, transversely through the cone shape 4.

The invention is based on the findings that the at least one thrombogenic fibre 3 of the medical implant 1 cannot stick to the inner wall of the cone shape 4 in the wet state in such a way that an aperture remains in the tapered region of the cone shape 4, if the thrombogenic fibre 3 extends transversely through the cone shape 4.

In the primary shape the base body 2 has an elongated shape so that it can be implanted into the human or animal body by means of a minimally invasive catheter technique. In this primary shape the base body 2 has a large ratio of longitudinal expansion to transverse expansion.

When leaving the catheter 12 used for implantation, the base body 2 preferably assumes autonomously the secondary shape, in which the medical implant 1 formed from the base body 2 closes the defect aperture, the vessel, the organ path or the other body aperture in the human or animal body. In this secondary shape the base body 2 has a smaller ratio of longitudinal expansion to transverse expansion than in the primary shape.

A cone shape 4 in the sense of the invention comprises an extended region 5 and a tapered region 6. The cone shape 4 thus corresponds to a funnel shape. The extended region 5 of the cone shape 4 is arranged at the distal end 7 of the medical implant 1, and the region 6 of the cone shape which is tapered is arranged at the proximal end of the medical implant 1. Distal in the sense of the invention is the region 7 of the medical implant 1 facing towards the middle of the body and proximal in the sense of the invention is the region of the medical implant 1 facing away from the middle of the body.

Furthermore, the design of the medical implant 1 according to the invention has a reduced hemolysis risk because the number of thrombogenic fibres 3 used has been significantly reduced. The loose ends of the thrombogenic fibres 3 can contribute to a destruction of erythrocytes, which is a main factor for hemolysis.

The at least one thrombogenic fibre 3 is connected to the base body 2 at at least two points. Such a configuration results in a simple manner to the fact that the at least one thrombogenic fibre 3 extends in the secondary shape of the base body 2 at least once transversely through the cone shape 4. Furthermore, the at least one thrombogenic fibre 3 runs in the primary shape of the base body 2 almost parallel to the base body 2 so that the at least one thrombogenic fibre 3 has almost no influence on the diameter of the medical implant 1 in the primary shape. Preferably, the at least one thrombogenic fibre 3 in the primary shape of the base body 2 protrudes at most 0.5 cm from the base body 2. The diameter of the medical implant 1 in the primary shape is particularly important for the minimally invasive implantation since the diameter of the medical implant 1 decisively influences the size of the catheter 12 to be used. Preferably, the at least one thrombogenic fibre 3 is connected to the base body 2 at more than two points. Thus, the at least one thrombogenic fibre 3 is arranged in a wavy manner on or around the base body 2 in the primary shape of the base body 2, and the regions of the at least one thrombogenic fibre 3 which are not connected to the base body 2 extend transversely through the cone shape in the secondary shape.

In a particularly preferred variant of the invention the wave-shaped sections of the thrombogenic fibre 3 are arranged on one side of the base body.

According to a further variant of the invention the base body 2 of the medical implant 1 comprises at least two thrombogenic fibres 3, which are each connected to the base body 2 at at least two points.

Advantageously, the base body 2 of the medical implant 1 consists of a shape memory material, in particular of nitinol or a plastic with a shape memory. The use of a shape memory material ensures that the medical implant 1, in particular its base body 2, transforms from the primary shape into the secondary shape in a predetermined manner. This is particularly advantageous for implantation by means of a minimally invasive catheter technique.

The base body 2 of the medical implant 1 of FIG. 1 is formed from a wire-like element 8 and is shaped like a helix. The wire-like element 8 of the base body 2 is thus formed into a coil. A base body 2 constructed as a coil has a high flexibility in the longitudinal direction as well as in the radial direction, with a simultaneous sufficient stability for closure of the defect aperture, the vessel, the organ path or the other aperture in the human or animal body.

In the exemplary embodiment according to FIG. 1 the at least one thrombogenic fibre 3 consists of a plastic fibre, for example selected from the group comprising absorbing and non-absorbing materials, natural and synthetic substances, in particular polyesters, polyamides, polypropylene, polybutyl esters, expanded polytetrafluoroethylene (ePTFE), polyvinyldifluoroethylene (PVDF), nylon, linen, silk, catgut.

Figure 2:
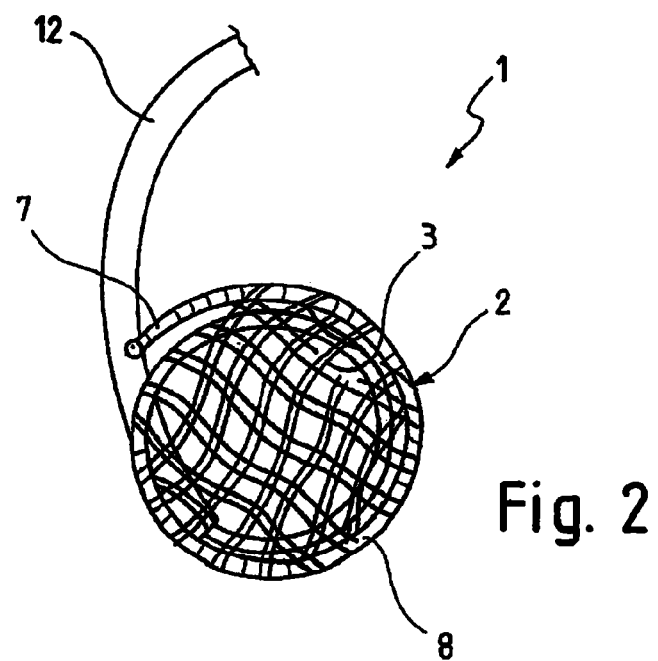
FIG. 2 is a perspective view of the medical implant from FIG. 1 during a transition from the primary shape into a secondary shape.

FIG. 2 shows a perspective view of the medical implant 1 from FIG. 1 during a transition from the primary shape into a secondary shape. For this purpose, the base body 2 of the medical implant 1 coils in such a way during exiting the catheter 12 used for implantation that the base body 2 forms a cone shape 4. The cone shape 4 comprises an extended region 5 and a tapered region 6. Upon exiting the catheter 12 the base body 2 coils itself from its distal end 7 and initially forms the extended region 5 of the cone shape 4. This configuration is illustrated in FIG. 2.

In the further course of the implantation the base body 2 is pushed further out of the catheter 12 and the base body coils or folds further from the primary shape into the secondary shape, that is, from an elongated shape into the cone shape 4. FIG. 3 shows a perspective view of the medical implant 1 from FIGS. 1 and 2 in the secondary shape, that is, after the proximal end of the base body 2 has also left the catheter 12. The view from FIG. 3 shows the medical implant 1 in a plan view towards the extended region 5. The tapered region 6 is therefore located centrally in the shown medical implant 1. FIG. 3 shows in particular that the at least one thrombogenic fibre 3 forms a net-like structure in the cone shape 4.

FIG. 4 shows a further perspective view of the medical implant 1 from FIG. 3 in the secondary shape. This view corresponds to a side view of the medical implant 1. FIG. 3 shows that the coiled secondary shape has a first tapered region 9, adjoining at its end a cylindrical region 11 with a smaller diameter and a third region 10 extending at least partially around the outside of the first tapered region 9 in a direction towards the end 7 with a larger diameter. The cone shape 4 thus consists of two funnels inserted into each other.

The medical implant 1 of FIGS. 1 to 4 has a diameter in the extended region 5 between 2.0 and 20.0 mm in the secondary shape, preferably between 8.0 and 16.0 mm. In the tapered region 6 of the medical implant 1 the medical implant 1 in the secondary shape has a diameter between 1.0 and 10.0 mm, preferably between 6.0 and 8.0 mm. The cylindrical section 11 has a diameter between 1.0 and 7.0 mm, preferably between 5.0 and 6.5 mm. The dimensions of the medical implant 1 are adapted to the defect aperture, the vessel, the organ path or the other aperture to be closed.

Figure 5:
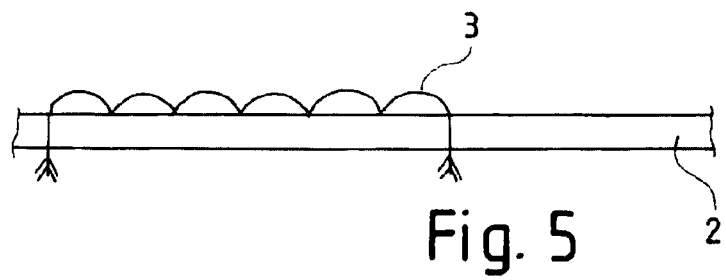
FIG. 5 is a schematic partial view of a first embodiment of the invention in a primary shape.
Figure 6:
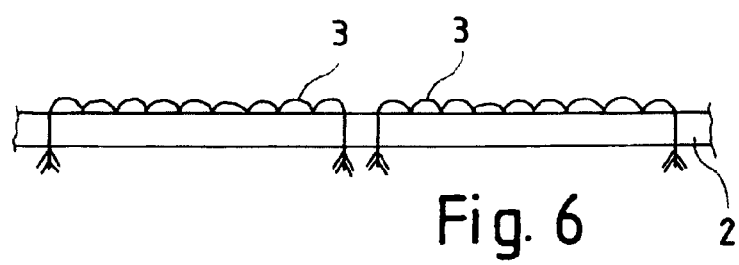
FIG. 6 is a schematic partial view of a second embodiment of the invention in a primary shape.
Figure 7:
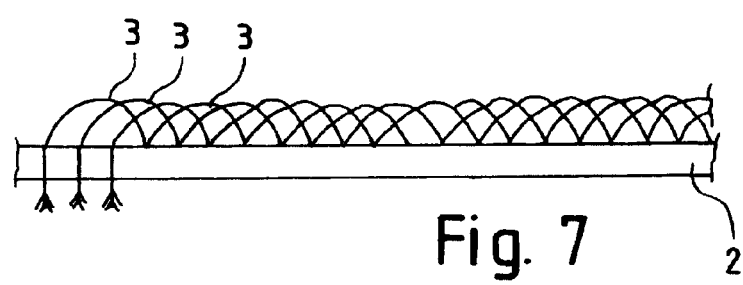
FIG. 7 is a schematic partial view of a third embodiment of the invention in a primary shape.
Figure 8:
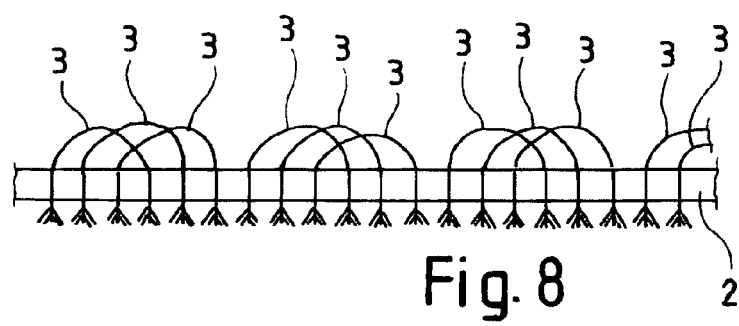
FIG. 8 is a schematic partial view of a fourth embodiment of the invention in a primary shape.

FIG. 5 shows a schematic partial view of a first embodiment according to the invention in a primary shape; FIG. 6 shows a schematic partial view of a second embodiment according to the invention in a primary shape; FIG. 7 shows a schematic partial view of a third embodiment according to the invention in a primary shape; and FIG. 8 shows a schematic partial view of a fourth embodiment according to the invention in a primary shape. The partial views from FIGS. 5 to 8 each show a section of a base body 2 of a medical implant 1 according to the invention and arranged thereon at least one thrombogenic fibre 3.

According to FIG. 5 a thrombogenic fibre 3 is arranged on the base body 2. The thrombogenic fibre 3 consists of a plurality of individual filaments, thereby improving the flexibility of the thrombogenic fibre 3. At the end points the thrombogenic fibre is attached to the base body 2 such that the thrombogenic fibre runs through the base body 2 so that the individual filaments of the thrombogenic fibre 3 protrude from the base body. Alternatively, the thrombogenic fibre 3 could also be fixed within the base body 2. Furthermore, the thrombogenic fibre 3 is connected to the base body 2 at five additional locations. In the embodiment according to FIG. 5 the thrombogenic fibre 3 is connected to the base body 2 at these intermediate connection points within the base body 2. Alternatively, these connecting points can also be formed like the end connection points so that the thrombogenic fibre 3 also runs through the base body 2 at these intermediate connection points. Advantageously, the thrombogenic fibre 3 is arranged at least in the region of the distal end 7 of the base body 2.

In the embodiment according to FIG. 6 two thrombogenic fibres 3 are arranged on the base body 2. These thrombogenic fibres 3 are each connected at their ends to the base body 2 such that the thrombogenic fibre 3 runs through the base body 2 and is connected to the inner of the base body at eight intermediate connection points. However, the type of connection between the thrombogenic fibre 3 and the base body 2 is basically freely selectable. The two thrombogenic fibres 3 of the embodiment of FIG. 6 are arranged side by side and do not overlap.

According to the embodiment of FIG. 7 three thrombogenic fibres 3 are arranged on the base body 2. As described with respect to the embodiments of FIGS. 5 and 6 the thrombogenic fibres 3 are connected to the base body 2 at their ends and at a plurality of intermediate points. The embodiment according to FIG. 7 differs from the previous embodiments according to FIGS. 5 and 6 in that the individual thrombogenic fibres 3 are arranged on the base body 2 in interlaced relationship.

According to the embodiment of FIG. 8 three thrombogenic fibres 3 are connected to the base body 2, which are interlaced with each other, wherein the thrombogenic fibres 3 are only connected at their ends to the base body 2. Accordingly a new arrangement consisting of three mutually entangled thrombogenic fibres 3 is arranged on the base body 2.

In the embodiments according to FIGS. 5 to 8 the connecting points of the respective thrombogenic fibres 3 are spaced from each other, preferably at a regular distance.

The individual embodiments according to FIGS. 5 to 8 can also be combined with one another. In particular, the number of the thrombogenic fibres 3, the number of connecting points between the thrombogenic fibre 3 and the base body 2, the configuration of the connection between the thrombogenic fibre 3 and the base body, the type and configuration of entanglement of thrombogenic fibres 3 and so on is freely selectable within the scope of the claims by the skilled person during implementation of the present invention.

LIST OF REFERENCES 1 medical implant
2 base body
3 thrombogenic fiber
4 cone shape
5 extended region
6 tapered region
7 distal end
8 proximal end 9 first cone region
10 third region
11 cylindrical region
12 catheter

What is claimed is:

1. A medical implant for closure of a defect aperture, a vessel, an organ path or another aperture in a human or animal body, comprising:
   a base body,
   at least two fibres, wherein the at least two fibres comprise a first fibre and a second fibre,
   wherein the base body is reversibly transformable against elastic material forces from a secondary shape into a primary shape,
   wherein in the primary shape the base body has an elongated shape and in the secondary shape is at least partially coiled and comprises a cone shape,
   wherein the at least two fibres are connected to the base body such that the at least two fibres in the secondary shape form a net-like structure in the cone shape;
   wherein the at least two fibres are connected to the base body such that the first fibre and the second fibre each form at least two half-loops on the base body, wherein each half-loop of the at least two half-loops formed by each of the first fibre and the second fibre has opposing ends connected to the base body and each half-loop is spaced from the base body between the opposing ends to form a closed loop with the base body;
   wherein, in the secondary shape, the at least two half-loops formed by each of the first fibre and the second fibre cross each other to form at least a portion of the net-like structure;
   wherein, in the primary shape, the at least two half-loops formed by each of the first fibre and the second fibre are arranged on different sides of the base body from each other; and
   wherein, in the primary shape, at least one of the at least two half-loops formed by the first fibre and at least one of the at least two half-loops formed by the second fibre are arranged at the different sides of the base body relative to one another as to form at least one whole loop.

2. The medical implant according to claim 1, wherein at least one fibre of the at least two fibres is connected to the base body at at least two connecting points.

3. The medical implant according to claim 2, wherein the at least one fibre of the at least two fibres is connected to the base body at more than two connecting points.

4. The medical implant according to claim 1, wherein the at least two fibres are each connected to the base body at at least two connecting points.

5. The medical implant according to claim 4, wherein the at least two connecting points of the respective at least two fibres are spaced from one another.

6. The medical implant according to claim 1, wherein the base body is formed of a material with a shape memory.

7. The medical implant according to claim 6, wherein the material with the shape memory comprises at least one of nitinol or plastic.

8. The medical implant according to claim 1, wherein the base body is formed from a wire-like element, wherein the base body has the form of a helix.

9. The medical implant according to claim 1, wherein at least one fibre of the at least two fibres is a thrombogenic fibre.

10. The medical implant according to claim 1, wherein at least one fibre of the at least two fibres is formed of at least one of plastic, linen, silk or catgut.

11. The medical implant according to claim 10, wherein at least one fibre of the at least two fibres is formed of plastic and the plastic comprises at least one of polyester, polyamide, polypropylene, polybutyl ester, polytetrafluoroethylene, polyvinyldifluoroethylene or nylon.

12. The medical implant according to claim 1, wherein the medical implant in the secondary shape has a diameter between 2.0 and 20.0 mm in an extended region.

13. The medical implant according to claim 1, wherein the medical implant in the secondary shape has a diameter between 1.0 and 10.0 mm in a first tapered region.

14. The medical implant according to claim 1, wherein the medical implant in the secondary shape has a diameter between 8.0 and 16.0 mm in an extended region.

15. The medical implant according to claim 1, wherein the medical implant in the secondary shape has a diameter between 6.0 and 8.0 mm in a first tapered region.

16. The medical implant according to claim 1, wherein the at least two half-loops formed by each of the first fibre and the second fibre which cross each other to form at least a portion of the net-like structure are transverse to one another.

17. The medical implant according to claim 1, wherein, in the primary shape, the at least two half-loops formed by each of the first fibre and the second fibre which are arranged on the different sides of the base body from each other are arranged on opposite sides of the base body.

* * * * *